United States Patent [19]
Garton et al.

[11] Patent Number: 5,877,358
[45] Date of Patent: Mar. 2, 1999

[54] ALCOHOL HYDROGENATION WITH INTERMEDIATE RECYCLE

[75] Inventors: Ronald D. Garton; Donald Q. Brown; Magdiel Agosto, all of Baton Rouge, La.

[73] Assignee: Exxon Chemical Patents Inc., Houston, Tex.

[21] Appl. No.: 717,980

[22] Filed: Sep. 23, 1996

[51] Int. Cl.$^6$ .................................................. C07C 29/14
[52] U.S. Cl. ............................................................. 568/882
[58] Field of Search ................................. 568/881, 814, 568/862, 882

[56] References Cited

U.S. PATENT DOCUMENTS

| | | | |
|---|---|---|---|
| 4,426,541 | 1/1984 | King | 568/881 |
| 4,451,677 | 5/1984 | Bradley et al. | 568/881 |
| 4,658,068 | 4/1987 | Hanin . | |
| 4,960,960 | 10/1990 | Harrison et al. | 568/881 |
| 5,030,774 | 7/1991 | Oswald et al. | 562/885 |
| 5,093,535 | 3/1992 | Harrison et al. . | |

Primary Examiner—José G. Dees
Assistant Examiner—Barbara Badio
Attorney, Agent, or Firm—John F. Hunt; Andrew B. Griffis

[57] ABSTRACT

In the process of hydrogenating a crude aldehyde product formed from the oxo process into a crude alcohol product, which process includes: feeding the crude aldehyde product into a first reactor which contains a hydrogenation catalyst, thereby forming a first hydrogenated product; feeding the first hydrogenated product from the first reactor through at least one intermediate reactor, each intermediate reactor being connected in series and containing a hydrogenation catalyst, thereby forming at least one intermediate hydrogenated product; and feeding the intermediate hydrogenated product from a last intermediate reactor to a final reactor which contains a hydrogenation catalyst, thereby forming the crude alcohol product; the improvement including a step wherein: at least a portion of the first hydrogenated product is recycled to the first hydrogenation reactor; or at least a portion of the intermediate hydrogenated product is recycled to the first hydrogenation reactor or an intermediate reactor upstream of the intermediate reactor from which the intermediate hydrogenated product is removed.

13 Claims, 3 Drawing Sheets

ALCOHOL HYDROGENATION WITH INTERMEDIATE RECYCLE

The present invention relates generally to the production of oxo alcohols from a crude hydroformylation aldehyde product. In particular, it relates to the recycle of alcohol hydrogenation intermediates to enhance the yield and quality of oxo alcohols produced.

BACKGROUND OF THE INVENTION

Hydroformylation reactions involve the preparation of oxygenated organic compounds by the reaction of carbon monoxide and hydrogen (synthesis gas) with carbon compounds containing olefinic unsaturation. The reaction is typically performed in the presence of a carbonylation catalyst and results in the formation of compounds, for example, aldehydes, which have one or more carbon atoms in their molecular structure than the starting olefinic feedstock. By way of example, higher alcohols may be produced in the so-called "oxo" process by hydroformylation of commercial $C_5$ to $C_{12}$ olefin fractions to an aldehyde-containing oxonation product, which on hydrogenation yields the corresponding $C_6$ to $C_{13}$ saturated alcohols. The oxo process is the commercial application of the hydroformylation reaction for making higher aldehydes and alcohols from olefins. The crude product of the hydroformylation reaction will typically contain catalyst, aldehydes, alcohols, unreacted olefin feed, synthesis gas and by-products.

The oxo process is well known in the art and is generally described in detail in Kirk-Other, Encyclopedia of Chemical Technology, Volume 16, 3rd edition, John Wiley & Sons, pp. 637–53, 1981. The teachings of U.S. Pat. No. 5,237,105 to Summerlin in regard to the oxo process are also incorporated herein by reference.

Prior to the hydrogenation step, the crude product of the oxo process is generally treated to remove the dissolved cobalt catalyst, which for reasons of economy may be recycled to the oxo reactor.

"Demetalled" hydroformylation reaction product or crude oxo aldehyde product is the reaction product which is substantially depleted of the transition metal cobalt catalyst required for the hydroformylation reaction. Such crude oxo aldehyde product will generally contain cobalt in an amount of from about 0.05 to 3.0 wt. %, calculated as elemental cobalt. The concentration of aldehyde in the crude oxo aldehyde product is generally from about 40 to 90 wt. %.

The next step in the oxo process is the hydrogenation of the crude oxo aldehyde product which is typically carried out in the presence of hydrogen and at pressures of about 6.89 MPa to 31.00 MPa (1000 to 4500 psig) using a hydrogenation catalyst.

The crude product of the oxo process is recovered then and, optionally, treated by known means to hydrogenate the aldehydes to form additional quantities of the corresponding oxo alcohols. These oxo alcohols, in turn, are widely used as chemical intermediates in the manufacture of plasticizers, detergents, solvents and the like.

The present inventors have developed a unique process which is capable of producing a higher yield of alcohols, as well as minimizing the amount of acid byproducts and dimer materials produced during the hydrogenation of oxo aldehydes. The present inventors have discovered that when hydrogenation is performed on a sulfided molybdenum-based catalyst such as NiMo, CoMo, NiCoMo, Mo and mixtures thereof, a higher yield and quality of alcohols can be obtained by recycling the output of one or more of the serially connected hydrogenation tank reactors back to the crude oxo aldehyde feedstream or, optionally, into a hydrogenation tank reactor connected in series with and preceding the hydrogenation tank reactor from which the recycle stream is taken.

Other and further objects, advantages and features of the present invention will be understood by reference to the following specification in conjunction with the annexed drawings.

SUMMARY OF THE INVENTION

A process is disclosed for hydrogenating a crude oxo aldehyde product formed by the hydroformylation of an olefinic feedstock with synthesis gas in the presence of a catalyst, which includes the following steps: feeding the crude oxo aldehyde product and/or a recycled partially hydrogenated product to a first hydrogenation reactor wherein the crude oxo aldehyde product is converted to a first partially hydrogenated product; feeding the first partially hydrogenated product from the first hydrogenation reactor to a second hydrogenation reactor wherein the first partially hydrogenated product is converted to a second partially hydrogenated product; and feeding at least part of the second partially hydrogenated product from the second hydrogenation reactor to the crude oxo aldehyde product upstream of the first hydrogenation reactor, which process generates an oxo alcohol product having higher yield and quality than a process that does not recycle partially hydrogenated product.

In this process, the first partially hydrogenated product may be fed from the first hydrogenation reactor to the second hydrogenation reactor via at least one intermediate hydrogenation reactor, or part of the second hydrogenated product may be fed from the second hydrogenation reactor to at least one downstream hydrogenation reactor.

Degassing steps for degassing the liquid hydrogenation product and exhausting the gas from the system prior to recycling the liquid hydrogenation product with the crude oxo aldehyde product are also disclosed. In this process, the catalyst is a sulfided catalyst selected from the group consisting of NiMo, CoMo, NiCoMo, Mo and mixtures thereof, and may further include a carbonaceous support. The ratio of the recycled second partially hydrogenated product to the aldehyde product is approximately 10:1, more preferably 3:1.

The additional step of feeding the crude oxo alcohol product into a subsequent plug flow reactor to produce a high yield crude oxo alcohol product is also disclosed.

A related process is also disclosed for hydrogenating a crude oxo aldehyde product formed by the hydroformylation of an olefinic feedstock with synthesis gas in the presence of a catalyst, which includes the following steps: feeding the crude oxo aldehyde product to a first hydrogenation reactor wherein the crude oxo aldehyde product is converted to a first partially hydrogenated product; feeding the first partially hydrogenated product from the first hydrogenation reactor to a second hydrogenation reactor wherein the first partially hydrogenated product is converted to a second partially hydrogenated product; feeding the second partially hydrogenated product from the second hydrogenation reactor to a third hydrogenation reactor wherein the second partially hydrogenated product is converted to a third partially hydrogenated product; and feeding at least part of the third partially hydrogenated product from the third hydrogenation reactor to the first hydrogenated product stream upstream of the third hydrogenation reactor, which process generates an oxo alcohol product having higher yield and quality than a process that does not recycle partially hydrogenated product.

The first partially hydrogenated product may be fed from the first hydrogenation reactor to the second hydrogenation reactor via at least one intermediate hydrogenation reactor. In addition, part of the third hydrogenated product is fed from the third hydrogenation reactor to at least one downstream hydrogenation reactor. Additional steps for degassing the liquid hydrogenation product prior to recycling with the crude oxo aldehyde product and exhausting the gas from the system are also disclosed.

In the process of hydrogenating a crude aldehyde product formed from the oxo process into a crude alcohol product, which process includes: feeding the crude aldehyde product into a first reactor which contains a hydrogenation catalyst, thereby forming a first hydrogenated product; feeding the first hydrogenated product from the first reactor through at least one intermediate reactor, each intermediate reactor being connected in series and containing a hydrogenation catalyst, thereby forming at least one intermediate hydrogenated product; and feeding the intermediate hydrogenated product from a last intermediate reactor to a final reactor which contains a hydrogenation catalyst, thereby forming the crude alcohol product; the improvement including a step wherein at least a portion of the intermediate hydrogenated product is recycled to the first hydrogenation reactor or an intermediate reactor upstream of the intermediate reactor from which the intermediate hydrogenated product is removed.

The additional step of feeding the crude alcohol product into a plug flow reactor, thereby increasing the oxo alcohol concentration of the crude alcohol product, is also disclosed, as is the process wherein the final reactor is a plug flow reactor, thereby increasing the oxo concentration of the crude alcohol product. The process may further include a step mixing hydrogen gas with the crude aldehyde product, and feeding hydrogen gas into the final reactor.

DESCRIPTION OF THE PREFERRED EMBODIMENTS

Figure 1:
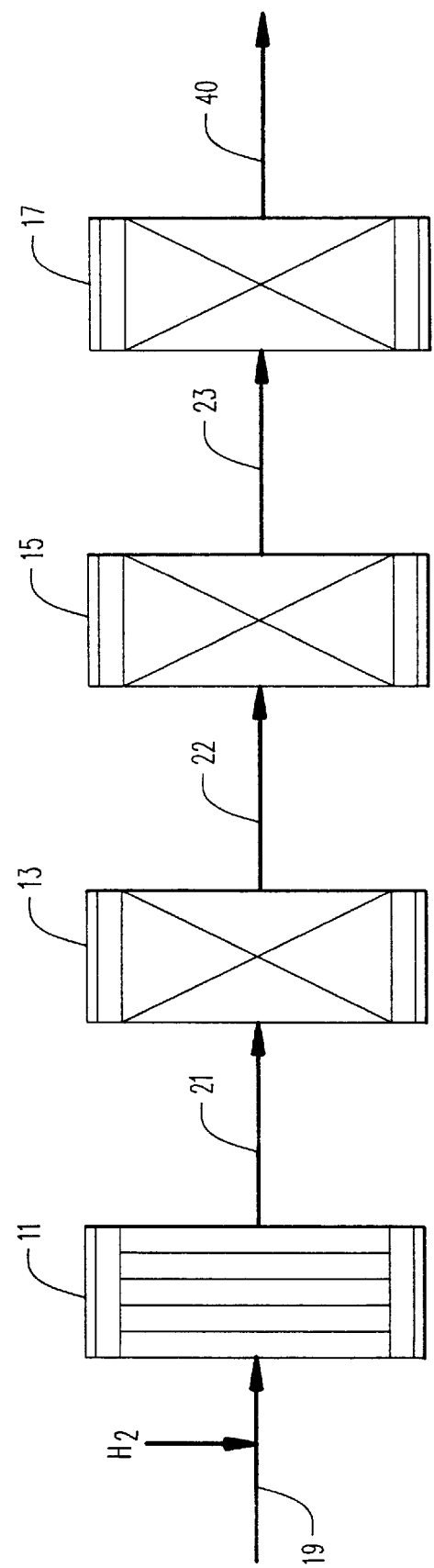
FIG. 1 is a schematic representation of the prior art process wherein oxo alcohols are formed from demetalled crude oxo aldehyde product.

FIG. 1 depicts the standard hydrogenation process employed in the art. Several reactor tanks (11, 13, 15, 17) are aligned in series and interconnected via conduits 21, 22 and 23, respectively. This series of tanks allows for easy replacement of the catalyst during operation when hydrogenation activity falls below a preset level. Tank 11 receives the crude oxo aldehyde feed from the hydroformylation reactors and subsequent demetallization reactors via conduit 19. Hydrogen in the form of $H_2$ is also fed into conduit 19. Reactor tank 11 contains a sulfided bimetallic molybdenum oxide catalyst supported on alumina. The crude oxo aldehyde feed flows over the catalyst bed and undergoes partial hydrogenation. This partially hydrogenated product is fed via conduit 21 to tank 13. The process is repeated through tanks 15 and 17 and results in a crude alcohol product passing from tank 17 via conduit 40.

Figure 2:
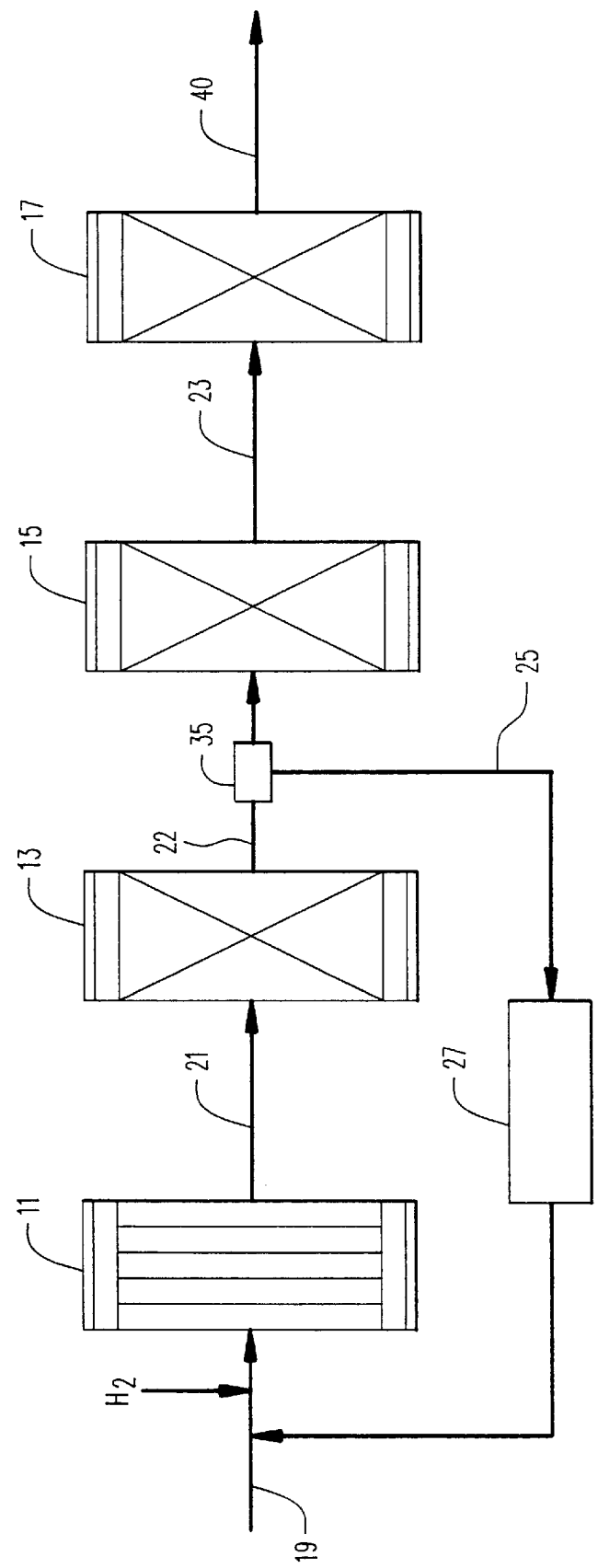
FIG. 2 is a schematic representation of the process according to a preferred embodiment of the present invention wherein crude aldehyde product is hydrogenated by passing through a series of hydrogenation reactors, wherein partially hydrogenated crude aldehyde product is recycled from an intermediate hydrogenation reactor via a degasser to the crude aldehyde product feedstream.

The process of the present invention is depicted in FIG. 2. The catalyst used in the present invention has high activity and durability. Thus, the ability to replace the catalyst frequently is not the controlling consideration in the design. The hydrogenation step in this preferred embodiment comprises a series of interconnected tank reactors (11, 13, 15, 17) similar to those of the prior art. A crude oxo aldehyde feed and a hydrogen feed are carried via conduit 19 into tank reactor 11 and flow over a catalyst bed therein containing a sulfided molybdenum-based catalyst on a carbonaceous support. The crude oxo aldehyde is partially hydrogenated, and this partially hydrogenated product is fed in series via conduits 21, 22 and 23 to tank reactors 13, 15 and 17 respectively. After the partially hydrogenated product undergoes further hydrogenation on the catalyst bed contained in tank reactors 13 and 15, the effluent taken from tank 13 via conduit 22 is bifurcated. Part of the effluent from tank 13 is fed via conduit 22 to tank reactor 15 to undergo further hydrogenation, while the remaining portion is diverted via conduit 25 through pump 27 back to conduit 19, where it is admixed, preferably at a ratio of 10:1, and most preferably 3:1 (crude oxo aldehyde feed to recycled partially hydrogenated alcohol), with the crude oxo aldehyde feed and is recycled back into tank reactor 11 to undergo further hydrogenation. The partially hydrogenated product from reactor 15 passes through conduit 23 to a plug flow reactor 17 which produces a commercial grade oxo alcohol via conduit 40. The ultimate alcohol product derived through this process has higher alcohol yield (on the order of 10 wt % higher yield), fewer acid byproducts and fewer dimer components than that produced in the hydrogenation process depicted in FIG. 1. In this preferred embodiment, the effluent from tank 13 is fed via conduit 22 through hot gas separator or degasser 35 before it is bifurcated. Degasser 35 separates the effluent into two components: substantially gas-free liquid that is diverted via conduit 25 for recycling, and a gas-liquid mixture sent via conduit 22 to tank 15. The substantially gas-free liquid has been stripped of the associated free gas. Some dissolved gas may remain in the liquid, however.

It will be readily apparent that the number of tank reactors used and the location of the conduit diverting the partially hydrogenated product, as well as the location of the reintroduction of the partially hydrogenated product, may all be varied without deviating from the disclosure of the present invention. The quality and yield of the alcohol product will be improved by recycle of partially hydrogenated intermediates at any stage of the disclosed hydrogenation process.

Figure 3:
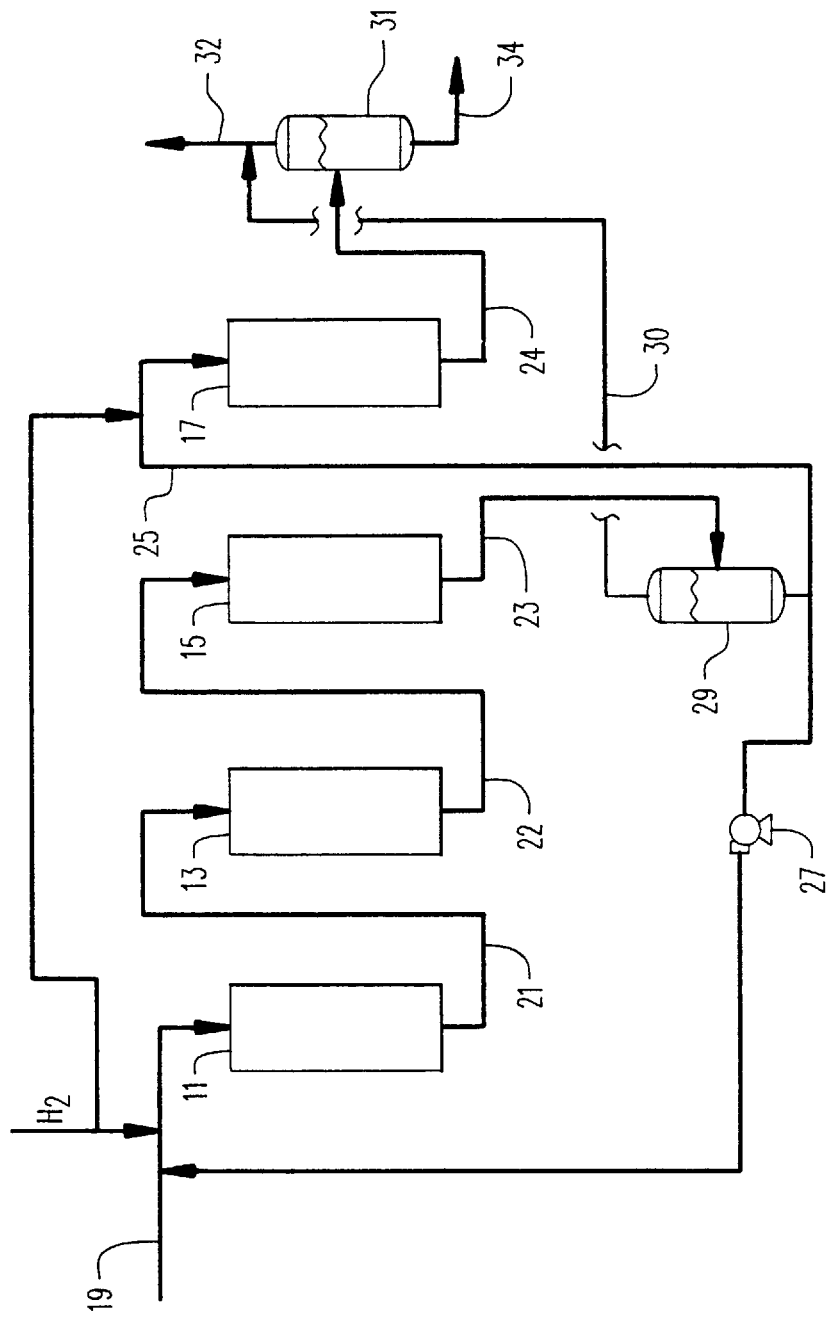
FIG. 3 is a schematic representation of an additional preferred embodiment of the present invention incorporating alternative degassing steps.

FIG. 3 depicts an alternate preferred embodiment of the present invention, wherein an alternate degassing step is incorporated in the recycle of the partially hydrogenated product. Here, the partially hydrogenated alcohol intermediate is recycled from reactor tank 15 via conduit 23 under the power of pump 27. Degasser 29 is situated intermediate reactor tank 15 and pump 27. Degasser 29 separates the partially hydrogenated alcohol intermediate into a gas-poor partially hydrogenated alcohol stream (containing essentially no free gas, but a proportion of dissolved gas) to be recycled back to tank 11 and a gas-enriched stream which is passed via conduits 30 and 32 out of the system. Conduit 30 optionally conveys part of the gas-laden effluent from tank 15 to conduit 32 to be vented. Alternatively, conduit 25 can convey part of the gas-poor product of degasser 29 into tank 17, to which additional syn gas can be added. The recycling of a degassed partially hydrogenated alcohol stream improves the overall efficiency of the operation. The oxo alcohol product is taken from reactor 17 via conduit 24 and delivered to another degasser 31 which separates the oxo alcohol product into a gaseous stream which is taken overhead via conduit 32 and a commercial grade oxo alcohol product which is taken as bottoms via conduit 34.

What is claimed is:

1. A process for hydrogenating a crude oxo aldehyde product formed by the hydroformylation of an olefinic feedstock with synthesis gas in the presence of a catalyst, which comprises the following steps:

feeding said crude oxo aldehyde product and/or a recycled partially hydrogenated product to a first hydrogenation reactor wherein said crude oxo aldehyde product is converted to a first partially hydrogenated product;

feeding said first partially hydrogenated product from said first hydrogenation reactor to a second hydrogenation reactor wherein said first partially hydrogenated product is converted to a second partially hydrogenated product;

feeding at least part of said second partially hydrogenated product from said second hydrogenation reactor to said crude oxo aldehyde product upstream of said first hydrogenation reactor; and feeding a resulting crude oxo alcohol product into a subsequent plug flow reactor, which process generates an oxo alcohol product having higher yield and quality than a process that does not recycle partially hydrogenated product.

2. The process of claim 1, wherein said first partially hydrogenated product is fed from said first hydrogenation reactor to said second hydrogenation reactor via at least one intermediate hydrogenation reactor.

3. The process of claim 1, wherein part of said second hydrogenated product is fed from said second hydrogenation reactor to at least one downstream hydrogenation reactor.

4. The process of claim 1, further comprising the step of degassing said hydrogenation product prior to recycling with said crude oxo aldehyde product.

5. The process of claim 1, wherein said catalyst is a sulfided catalyst.

6. The process of claim 5, wherein said sulfided catalyst is selected from the group consisting of NiMo, CoMo, NiCoMo, Mo, and mixtures thereof.

7. The process of claim 5, wherein said sulfided catalyst further comprises a carbonaceous support.

8. The process of claim 1, wherein the ratio of said recycled second partially hydrogenated product to said aldehyde product is approximately 10:1.

9. A process for hydrogenating a crude oxo aldehyde product formed by the hydroformylation of an olefinic feedstock with synthesis gas in the presence of a catalyst, which comprises the following steps:

feeding said crude oxo aldehyde product to a first hydrogenation reactor wherein said crude oxo aldehyde product is converted to a first partially hydrogenated product;

feeding said first partially hydrogenated product via a first partially hydrogenated product stream from said first hydrogenation reactor to a second hydrogenation reactor wherein said first partially hydrogenated product is converted to a second partially hydrogenated product;

feeding said second partially hydrogenated product from said second hydrogenation reactor to a third hydrogenation reactor wherein said second partially hydrogenated product is converted to a third partially hydrogenated product;

feeding at least part of said third partially hydrogenated product from said third hydrogenation reactor to said first hydrogenated product stream upstream of said third hydrogenation reactor, and feeding a resulting crude oxo alcohol product into a subsequent plug flow reactor, which process generates an oxo alcohol product having higher yield and quality than a process that does not recycle partially hydrogenated product.

10. In the process of hydrogenating a crude aldehyde product formed from the oxo process into a crude alcohol product, which process comprises:

(a) feeding said crude aldehyde product into a first reactor which contains a hydrogenation catalyst, thereby forming a first hydrogenated product;

(b) feeding said first hydrogenated product from said first reactor through at least one intermediate reactor, each said intermediate reactor being connected in series and containing a hydrogenation catalyst, thereby forming at least one intermediate hydrogenated product;

(c) feeding said intermediate hydrogenated product from a last intermediate reactor to a final reactor which contains a hydrogenation catalyst, thereby forming said crude alcohol product; wherein:

(i) at least a portion of said first hydrogenated product is recycled to said first hydrogenation reactor; or (ii) at least a portion of said intermediate hydrogenated product is recycled to (A) said first hydrogenation reactor; or (B) an intermediate reactor upstream of the intermediate reactor from which said intermediate hydrogenated product is removed; and (d) feeding a resulting crude alcohol product into a plug flow reactor, thereby increasing the oxo alcohol concentration of said crude alcohol product.

11. In the process of hydrogenating a crude aldehyde product formed from the oxo process into a crude alcohol product, which process comprises:

(a) feeding said crude aldehyde product into a first reactor which contains a hydrogenation catalyst, thereby forming a first hydrogenated product;

(b) feeding said first hydrogenated product from said first reactor through at least one intermediate reactor, each said intermediate reactor being connected in series and containing a hydrogenation catalyst, thereby forming at least one intermediate hydrogenated product;

(c) feeding said intermediate hydrogenated product from a last intermediate reactor to a final reactor which contains a hydrogenation catalyst, thereby forming a crude alcohol product; wherein:

(i) at least a portion of said first hydrogenated product is recycled to said first hydrogenation reactor; or (ii) at least a portion of said intermediate hydrogenated product is recycled to
   (A) said first hydrogenation reactor; or
   (B) an intermediate reactor upstream of the intermediate reactor from which said intermediate hydrogenated product is removed, wherein said final reactor is a plug flow reactor, thereby increasing the oxo concentration of said crude alcohol product.

12. The process of claim 1, further comprising mixing hydrogen gas with said crude aldehyde product.

13. The process of claim 1, further comprising feeding hydrogen gas into said final reactor.

* * * * *